United States Patent [19]

King et al.

[11] Patent Number: 4,920,127

[45] Date of Patent: Apr. 24, 1990

[54] SUBSTITUTED INDOLES AND THEIR USE AS 5-HT₃ RECEPTOR ANTAGONISTS

[75] Inventors: Francis D. King; Karen A. Joiner, both of Harlow, England

[73] Assignee: Beecham Group p.l.c., England

[21] Appl. No.: 155,756

[22] Filed: Feb. 16, 1988

[30] Foreign Application Priority Data

Feb. 18, 1987 [GB] United Kingdom ............... 8703815
May 28, 1987 [GB] United Kingdom ............... 8712492
Aug. 8, 1987 [GB] United Kingdom ............... 8718844

[51] Int. Cl.⁵ .............. A61K 31/395; C07D 213/00; C07D 221/02; C07D 453/02
[52] U.S. Cl. .................. 514/278; 514/299; 514/305; 514/413; 514/414; 514/409; 540/543; 540/602; 546/15; 546/112; 546/133; 548/409; 548/411
[58] Field of Search .......... 546/15, 112, 133; 540/543, 602; 514/278, 299, 305, 409, 413, 414; 548/409, 411

[56] References Cited

FOREIGN PATENT DOCUMENTS

3445377A1 7/1985 Fed. Rep. of Germany ...... 546/133
2125398A 3/1984 United Kingdom ............... 546/133
2152049A 7/1985 United Kingdom ............... 546/133

OTHER PUBLICATIONS

J. Nilsson et al., "Some Quinnolidine Derivatives with Potential Antimalarial Activity", ACTA Pharmaceutica Suecica, 5, pp. 71–76 (1968).

Primary Examiner—Mary C. Lee
Assistant Examiner—J. Richter
Attorney, Agent, or Firm—James F. Haley, Jr.; David K. Barr; Doreen F. Shulman

[57] ABSTRACT

Compounds of formula (I), or a pharmaceutically acceptable salt thereof:

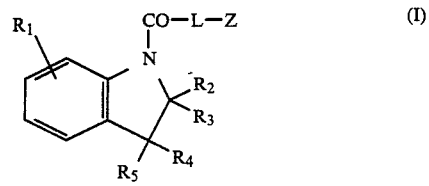

wherein
L is NH or O;
$R_1$ is hydrogen, fluoro or chloro;
$R_2$ and $R_5$ are independently hydrogen or $C_{1-6}$ alkyl or together are a bond; or
$R_2$ and $R_3$ and/or $R_4$ and $R_5$, together are $C_{2-7}$ polymethylene or $-(CH_2)_m-O-(CH_2)_x-$ where m and x. are 1 to 5 such that m+x is 2 to 6;
$R_4$ is $C_{1-7}$ acyl, $C_{1-6}$ alkoxycarbonyl, hydroxycarbonyl, aminocarbonyl optionally substituted by one or two $C_{1-6}$ alkyl groups, $CF_3$, $C_{1-6}$ alkyl substituted by $C_{1-6}$ alkoxy, $C_{1-6}$ alkylthio or by $C_{1-6}$ alkoxycarbonyl, or $R_4$ is phenyl or phenyl-$C_{1-4}$ alkyl optionally substituted in the phenyl ring by one or two of halogen, $C_{1-6}$ alkyl or $C_{1-6}$ alkoxy;
Z is a group of formula (a), (b) or (c).

9 Claims, No Drawings

SUBSTITUTED INDOLES AND THEIR USE AS 5-HT$_3$ RECEPTOR ANTAGONISTS

This invention relates to novel compounds having useful pharmacological properties, to pharmaceutical compositions containing them, to a process and intermediates for their preparation, and to their use as pharmaceuticals. GB Nos. 2100259A and 2125398A, and EP-A-158265 describe aryl amides and esters having an azabicyclic side chain and possessing 5-HT$_3$ receptor antagonist activity.

A class of novel, structurally distinct compounds has now been discovered. These compounds have 5-HT$_3$ receptor antagonist activity.

Accordingly, the present invention provides a compound of formula (I), or a pharmaceutically acceptable salt thereof:

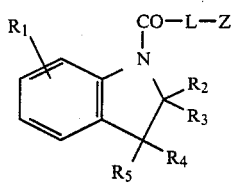

(I)

wherein
L is NH or O;
R$_1$ is hydrogen, fluoro or chloro;
R$_2$ and R$_5$ are independently hydrogen or C$_{1-6}$ alkyl or together are a bond; or
R$_2$ and R$_3$ and/or R$_4$ and R$_5$, together are C$_{2-7}$ polymethylene or—(CH$_2$)$_m$-O-(CH$_2$)$_x$— where m and x are 1 to 5 such that m+x is 2 to 6;
R$_4$ is C$_{1-7}$ acyl, C$_{1-6}$ alkoxycarbonyl, hydroxycarbonyl, aminocarbonyl optionally substituted by one or two C$_{1-6}$ alkyl groups, CF$_3$, C$_{1-6}$ aklyl substituted by C$_{1-6}$ alkoxy, C$_{1-6}$ alkylthio or by C$_{1-6}$ alkoxycarbonyl, or R$_4$ is phenyl or phenyl-C$_{1-4}$ alkyl optionally substituted in the phenyl ring by one or two of halogen, C$_{1-6}$ alkyl or C$_{1-6}$ alkoxy;
Z is a group of formula (a), (b) or (c)

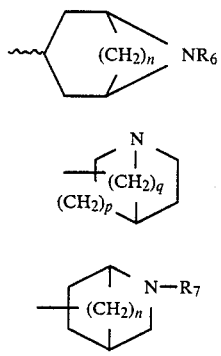

wherein
n is 2 or 3;
p is 1 or 2;
q is 1 to 3;
r is 1 to 3; and
R$_6$ or R$_7$ is C$_{1-4}$ alkyl.
Preferably L is NH.
R$_1$ is preferably hydrogen.

Examples of moieties in alkyl or alkyl containing groups in R$_2$ to R$_7$ include methyl, ethyl, n- and iso-propyl, n-, iso-, sec- and tert-butyl.

Suitable example of R$_2$ and R$_3$/R$_4$ and R$_5$ when joined include C$_2$, C$_3$, C$_4$, C$_5$ or C$_6$ polymethylene, preferably C$_2$, C$_3$, C$_4$ or C$_5$ polymethylene; or —(CH$_2$)$_{m^1}$-O-(CH$_2$)$_{x^1}$— wherein m$^1$ is 1 to 3 and x$^1$ is 1 to 3.

Examples of R$_4$ when C$_{1-7}$ acyl include C$_{2-7}$ alkanoyl and halo substituents for a phenyl group in R$_4$ include chloro, bromo and fluoro.

Preferably n is 2 and p, q and r are 1 or 2.

R$_6$/R$_7$ is preferably methyl or ethyl, most preferably methyl.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, lactic, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts include quaternary derivatives of the compounds of formula (I) such as the compounds quaternised by compounds R$_a$-T wherein R$_a$ is C$_{1-6}$ alkyl, phenyl-C$_{1-6}$ alkyl or C$_{5-7}$ cycloalkyl, and T is a radical corresponding to an anion of an acid. Suitable examples of R$_a$ include methyl, ethyl and n- and iso-propyl; and benzyl and phenethyl. Suitable examples of T include halide such as chloride, bromide and iodide.

Examples of pharmaceutically acceptable salts of compounds of formula (I) also include internal salts such as pharmaceutically acceptable N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realised that compounds of formula (I) may adopt an endo or exo configuration with respect to L. The endo configuration is preferred.

A group of compounds within formula (I) is of formula (II):

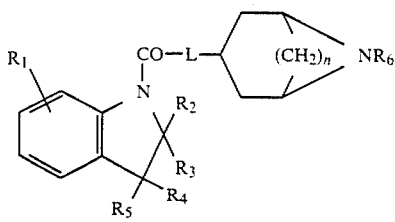

wherein the variables are as defined in formula (I).

Examples of the variables and preferred variables are as so described for corresponding variables in relation to formula (I).

A further group of compounds within formula (I) is of formula (III):

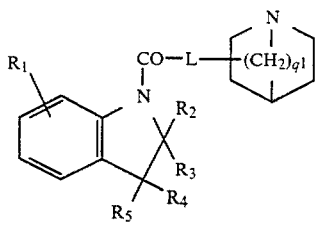

wherein $q^1$ is 1 or 2 and the remaining variables are as defined in formulae (I) and (II).

Examples of the variables and preferred variables are as so described for the corresponding variables in formula (I).

There is a further group of compounds within formula (I) of formula (IV):

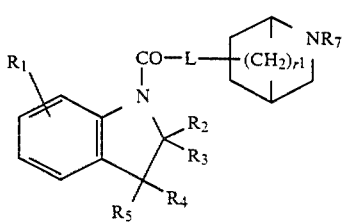

wherein $r^1$ is 1 or 2 and the remaining variables are as defined in formulae (I) and (II).

Examples of the variables and preferred variables are so described as the corresponding variables in formula (I).

The invention also provides a process for the preparation of a compound of formula (I), or a pharmaceutically acceptable salt thereof, which process comprises reacting a compound of formula (V):

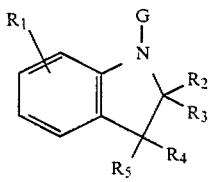

with a compound of formula (VI):

J—$Z^1$ (VI)

wherein

G is $COQ_1$, where $Q_1$ is a leaving group, or G is hydrogen; and, when G is $COQ_1$, J is $NH_2$, or OH or a reactive derivative thereof or, when G is hydrogen, J is a group containing an activated carbonyl group capable of forming a CO-L-linkage with the compound of formula (V); $Z^1$ is Z as defined or Z wherein $R_6/R_7$ is replaced by a hydrogenolysable protecting group; and the remaining variables are as hereinbefore defined; and thereafter optionally converting an $R_1$ group to another $R_1$ group, converting $Z^1$, when other than Z, to Z; converting $R_2$ and $R_4$ to other $R_2$ and $R_4$; and optionally forming an pharmaceutically acceptable salt of the resultant compound of formula (I).

Examples of leaving groups $Q_1$, displaceable by a nucleophile, include halogen such as chloro and bromo; $C_{1-4}$ alkoxy, such as $CH_3O$ and $C_2H_5O$—; PhO-; activated hydrocarbyloxy, such as $Cl_5C_6O$— or $Cl_3CO$-; succinimidyloxy; and imidazolyl. Preferably $Q_1$ is halogen, most preferably chloro.

If a group $Q_1$ is a halide or imidazolyl, then the reaction is preferably carried out at non-extreme temperatures in an inert non-hydroxylic solvent, such as benzene, dichloromethane, toluene, diethyl ether, tetrahydrofuran (THF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°-100° C., in particular 10°-80° C. are suitable.

If a group $Q_1$ is $C_{1-4}$ alkoxy, phenoxy, activated hydrocarbyloxy or succinimidyloxy then the reaction is preferably carried out in an inert solvent, such as toluene or dimethylformamide. In this instance, it is preferred that the group $Q_1$ is $Cl_3CO$— or succinimidyloxy and that the reaction is carried out in toluene at reflux temperature.

When J is OH or a reactive derivative thereof, the reactive derivative is often a salt, such as the lithium, sodium or potassium salt.

When G is hydrogen, J—$Z^1$ may be a compound of formula (VII) or (VIII) when L is NH; or of formula (IX) when L is O:

$$O=C=N-Z^1 \quad (VII)$$

$$\underset{Q_2-\overset{O}{\overset{\|}{C}}-NH-Z^1}{} \quad (VIII)$$

$$\underset{Q_3-\overset{O}{\overset{\|}{C}}-O-Z^1}{} \quad (IX)$$

wherein $Z^1$ is as hereinbefore defined, and $Q_2$ and $Q_3$ are leaving groups, preferably $Cl_3CO$ and Cl respectively.

When J—$Z^1$ is of formula (VII), the reaction is preferably carried out in an inert solvent, under conventional conditions at a temperature 0°-100° C.

$Q_2$ is a leaving group as defined for $Q_1$ hereinbefore; and the reaction is carried out in accordance with the conditions described herein for the reaction wherein G is $COQ_1$.

Examples of $Q_3$, displaceable by a nucleophile, include halogen, such as chloro and bromo; and activated hydrocarbyloxy, such as $Cl_5C_6O-$ and $Cl_3CO$.

If a group $Q_3$ is a halide, the reaction is carried out as described above for $Q_1$ halide.

If $Q_3$ is activated hydrocarbyloxy, the reaction is carried out as described for $Q_1$ activated hydrocarbyloxy.

It will be apparent that compounds of the formula (I) containing an $R_1$ group which is convertible to another $R_1$ group are useful novel intermediates. For example, a hydrogen substituent is convertible to a halogen substituent by halogenation.

$Z^1$ when other than Z may have a hydrogenolysable protecting group which is benzyl optionally substituted by one or two groups independently selected from halogen, $C_{1-4}$ alkoxy, $C_{1-4}$ alkyl or nitro. Such benzyl groups may, for example, be removed, when $R_1$ is not halogen, by conventional transition metal catalysed hydrogenolysis to give compounds of the formula (X):

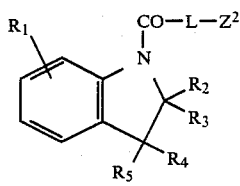
(X)

wherein $Z^2$ is of formula (d) or (e)

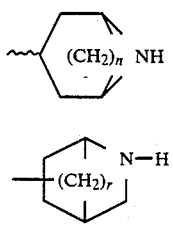

wherein the variables are as defined in formula (I).

This invention also provides a further process for the preparation of a compound of the formula (I) which comprises N-alkylating a compound of formula (X), and optionally forming a pharmaceutically acceptable salt, of the resulting compound of the formula (I).

This may be achieved by reaction of the compound of formula (X) with a compound $R_6Q_4$ wherein $R_6$ and $R_7$ are as hereinbefore defined and $Q_4$ is a leaving group.

Suitable values for $Q_4$ include groups displaced by nucleophiles such as Cl, Br, I, $OSO_2CH_3$, $OSO_2C_6H_4pCH_3$ or $OSO_3CH_3$.

Favoured values for $Q_4$ include Cl, Br and I.

The reaction may be carried out under conventional alkylation conditions for example in an inert solvent such as dimethylformamide in the presence of an acid acceptor such as potassium carbonate. Generally the reaction is carried out at non-extreme temperature such as at ambient or slightly above.

Alternatively, 'N-alkylation' may be effected under conventional reductive alkylation conditions when the group $R_6$ or $R_7$ in the compound of formula (I) contains a methylene group adjacent to the N-atom in the bicycle.

Interconverting $R_6$ or $R_7$ in the compound of the formula (X) before coupling with the compound of the formula (V) is also possible. Such interconversions are effected conveniently under the above conditions. It is desirable to protect any amine function with a group readily removable by acidolysis such as a $C_{2-7}$ alkanoyl group, before $R_6/R_7$ interconversion.

When $R_6$ or $R_7$ in the compound of formula (VI) contains a methylene group adjacent to the N-atom in the bicycle it is often convenient in the preparation of such a compound of formula (VI) to prepare the corresponding compound wherein the methylene group is replaced by —CO-, or for $R_6$ or $R_7$ is methyl, where the methyl group is replaced by alkoxycarbonyl. Such compounds may then be reduced using a strong reductant such as lithium aluminium hydride to the corresponding compound of formula (V).

The compounds of formula (VI) are known or are preparable analogously to, or routinely from, known compounds. Intermediates of formula (V) may be prepared as described in the descriptions hereafter, or by analogous methods thereto. Intermediates of formula (V) are novel and form an aspect of the invention.

Compounds of the formula (VI) wherein Z is of formula (c) may be prepared as described in European Patent Publication No. 115933 or by analogous methods thereto.

Compounds of the formula (X) are novel and form an aspect of the invention.

It will be realised that in the compound of the formula (I) the —CO-L-linkage may have an endo or exo orientation with respect to the ring of the bicyclic moiety to which it is attached. A mixture of endo and exo isomers of the compound of the formula (I) may be synthesised non-stereospecifically and the desired isomer separated conventionally therefrom e.g. by chromatography; or alternatively the endo and exo isomer may if desired be synthesised from the corresponding endo or exo form of the compound of the formula (VI).

Compounds of the formula (I) wherein $R_2$ and $R_5$ are both hydrogen may be converted to the corresponding compounds wherein $R_2$ and $R_5$ are a bond by conventional oxidation, and this is the preferred method when $R_2$ and $R_5$ are a bond. Compounds of the formula (I) wherein $R_2$ and $R_4$ are a bond may be converted to the corresponding compounds wherein $R_2$ and $R_5$ are hydrogen by reduction; however it is preferred that this is carried out on the compound of formula (V) wherein G is H prior to coupling.

Pharmaceutically acceptable salts of the compounds of this invention may be formed conventionally. The acid addition salts may be formed for example by reaction of the base compound of formula (I) with a pharmaceutically acceptable organic or inorganic acid.

The compounds of the present invention are 5-HT$_3$ receptor antagonists and it is thus believed may generally be used in the treatment or prophylaxis of migraine, cluster headaches and trigeminal neuralgia; emesis, in particular that of preventing cytotoxic agent or radiation induced nausea and vomiting; and visceral pain. Compounds which are 5-HT$_3$ receptor antagonists may also be potential use in the treatment of CNS disorders such as anxiety and psychosis; arrhythmia, obesity and gastrointestinal disorders, such as irritable bowel syndrome.

Examples of cytotoxic agents include cisplatin, doxorubicin and cyclophosphamide.

The compounds of the present invention may also have gastric motility enhancing activity, useful in the treatment of disorders such as retarded gastric emptying, dyspepsia, flatulence, oesophagal reflux and peptic ulcer.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as much may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparation may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of migraine, cluster headache, trigeminal neuralgia and/or emesis in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.1 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of migraine, cluster headache, trigeminal neuralgia and/or emesis.

The following Examples illustrate the preparation of compounds of formula (I); the following descriptions illustrate the preparation of intermediates.

DESCRIPTION 1

Spiro(cyclohexyl-1,3-indolenine)zinc chloride (D1)

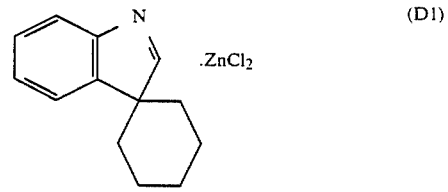

To a stirred solution of cyclohexaldehyde phenylhydrazone (3.6 g) in EtOH (25 ml) was added zinc chloride (5.0 g). The reaction mixture was then heated to reflux in a $N_2$ atmosphere for 3½ hours. The reaction mixture was cooled and acidified with 5 N HCl. A yellow gummy solid formed which was filtered off and dried to give the title compound as the zinc chloride salt (4.5 g, 78%).

DESCRIPTION 2

Spiro(cyclohexyl-3-indoline) (D2)

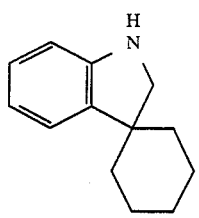 (D2)

Spiro(cyclohexyl-1,3-indolenine)zinc chloride salt (D1) (4.5 g) was hydrogenated at atmospheric pressure and at 30° C. in EtOH (125 ml) and glacial acetic acid (10 ml) over PtO$_2$ catalyst (0.5 g) for 20 hours. The catalyst was filtered off and the filtrate was evaporated to dryness. The residue was distilled at 0.1 mmHg and the fraction Bpt 60°–100° C. collected (0.77 g, 29%).

DESCRIPTION 3

Spiro(cyclohexyl-3-indoline)-1-carbonyl chloride (D3)

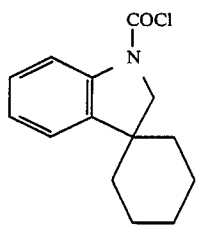 (D3)

To a stirred solution of spiro(cyclohexyl-3-indoline) (D2) (0.77 g) in CH$_2$Cl$_2$ (30 ml) at 0° C. under an N$_2$ atmosphere was added 12.5% phosgene in toluene solution (3.7 ml). After 10 minutes Et$_3$N (0.6 ml) was added. The reaction mixture was then stirred for 30 minutes, poured into pentane (300 ml) and washed with 5N H$_2$SO$_4$ (50 ml) followed by saturated brine solution (50 ml). The organic solution was dried over Na$_2$SO$_4$ and the solvent removed by rotary evaporation to yield the title compound (0.7 g, 68%).

DESCRIPTION 4

2,3-Dihydro-3-ethoxycarbonylindole (D4)

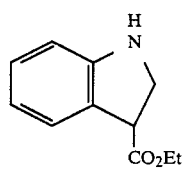 (D4)

Sodium (4.28 g) was added portionwise to a solution of indole-3-carboxylic acid (2 g) in ethanol (40 ml) which was heated under reflux. After all the sodium had reacted, the mixture was cooled to 50° C. and ethanolic-hydrogen chloride solution was added to neutral pH. Hydrogen chloride was bubbled through the suspension for 1.5 h which was heated under reflux. Reflux was continued for a further 1 h. The mixture was cooled, the solvent evaporated under reduced pressure and the solid was dissolved in water (30 ml). The aqueous phase was washed with diethyl ether (2×30 ml) then basified with solid potassium carbonate and the product extracted into dichloromethane. The organic phase was dried (Na$_2$SO$_4$), the solvent evaporated under reduced pressure and the residue purified via bulb to bulb distillation at 7 mmHg and 185° C. to give the title compound (D4) (1.25 g, 53%).

$^1$H-NMR (CDCl$_3$) 60 MHz. δ 7.65–6.55 (m, 4H); 4.50–3.55 (m, 6H); 1.25 (t, 3H).

DESCRIPTION 5

2,3-Dihydro-3-ethoxycarbonyl-3-methylindole (D5)

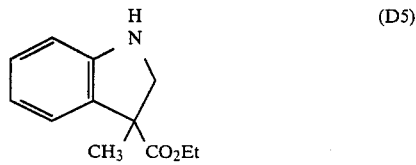 (D5)

To a solution of 2,3-dihydro-3-ethoxycarbonylindole (D4) (0.75 g) in dry tetrahydrofuran (20 ml) at −78° C. under an atmosphere of nitrogen, was added dropwise lithium diisopropylamide (2.4 ml (1.8M solution in hexane)). The mixture was stirred at −78° C. for a further 1 h and then methyliodide (0.26 ml) was added. The reaction mixture was allowed to warm to room temperature over 2 h. Water was added and then the product extracted into diethyl ether. The organic phase was dried (Na$_2$SO$_4$), the solvent evaporated under reduced pressure and the residue filtered through a short silica column, eluting with 40% 40/60 pet. ether/diethyl ether. This was further purified by distillation at reduced pressure to give the title compound (D5) (0.64 g, 80%).

$^1$H-NMR (CDCl$_3$) 60 MHz. δ 7.40–6.45 (m, 4H); 4.35–3.80 (m, 3H); 3.65 (bs, 1H); 3.20 (d, 1H); 1.50 (s, 3H); 1.25 (t, 3H).

DESCRIPTION 6

1-(2,3-Dihydro-3-ethoxycarbonyl)indolylcarbonyl chloride (D6)

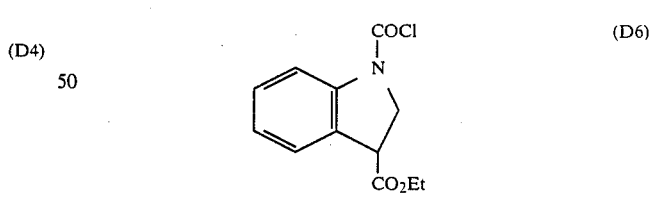 (D6)

To phosgene (2.4 ml (12.5% w/w solution in toluene)) in dry dichloromethane (50 ml) at 0° C. was added dropwise a solution of triethylamine (0.36 ml) and freshly distilled 2,3-dihydro-3-ethoxycarbonylindole (D4) (0.5 g) in dry dichloromethane (10 ml). The reaction mixture was then stirred at 0° C. for 1 h, and then poured into pentane (500 ml), washed with 5N sulphuric acid solution (10 ml) and brine (10 ml). The organic phase was dried (Na$_2$SO$_4$), the solvent evaporated under reduced pressure to give the title compound (D6) (0.55 g, 84%).

DESCRIPTION 7

1-(2,3-Dihydro-3-ethoxycarbonyl-3-methyl)indolylcarbonyl chloride (D7)

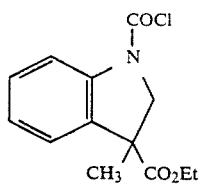

Following the procedure outlined in Description 6: reaction of 2,3-dihydro-3-ethoxycarbonyl-3-methylindole (D5) (0.64 g) with phosgene [2.8 ml (12.5% w/w solution in toluene)] and triethylamine (0.43 ml) afforded the title compound (D7) (0.8 g, 96%).

$^1$H-NMR (CDCl$_3$) 60 MHz. δ 8.00–6.95 (m, 4H); 4.85 (d, 1H); 4.40–3.75 (m, 3H); 1.65 (s, 3H); 1.25 (t, 3H).

DESCRIPTION 8

Spiro(cyclopropyl-3-indoline) (D8)

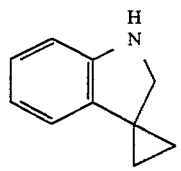

A solution of spiro(cyclopropyl-1,3'-indolenine) (0.6 g) (Johansen, Christie and Rapoport, J. Org. Chem., 46, 4918, 1981) in dry ether (50 ml) was treated with diisobutylaluminiumhydride (1.5 equivalents) at room temperature under a nitrogen atmosphere. The reaction was stirred at room temperature for one hour. Methanol (5 ml) was added and the mixture stirred for a further 10 minutes. A solution of potassium sodium tartrate (6.0 g) in water (50 ml) was then added with vigorous stirring. After 10 minutes the organic layer was separated, dried and the solvent evaporated to give the title compound (D8) (0.49 g, 80%).

$^1$H-NMR (CDCl$_3$) 60 MHz. δ 7.13–6.40 (m, 4H); 3.64 (s, 1H); 3.40 (s, 2H); 1.05–0.80 (m, 4H).

DESCRIPTION 9

Spiro(cyclopropyl-3-indoline)-1-carbonylchloride (D9)

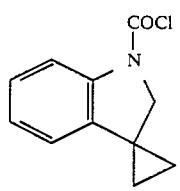

Following the procedure outlined in description 3, reaction of spiro(cyclopropyl-3-indoline) (D8) (0.49 g) with phosgene ]3.4 ml (12.5% w/w solution in toluene)] and triethylamine (0.55 ml) afforded the title compound (D9) (0.63 g, 90%).

DESCRIPTION 10

2,3-Dihydro-3-phenylindole (D10)

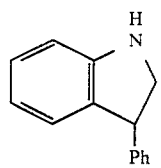

To a stirred suspension of 3-phenylindole (3.5 g) (GB 959,203; CA 61 10659 g) in dry trifluoroacetic acid (70 ml) at 0° C. under an atmosphere of nitrogen, was added dropwise triethylsilane (22.3 ml). The green solution was stirred at 0° C. for a further 0.25 h and then allowed to warm to ambient temperature and stirred for a further 1.5 h. The solvent was evaporated under reduced pressure, the residue dissolved in 5N HCl (15 ml) and washed with diethylether (30 ml). The aqueous phase was basified with potassium carbonate and the product extracted into dichloromethane (3×50 ml). The product was purified by distillation at reduced pressure to give the title compound (D10) (2 g, 57%).

$^1$H-NMR (CDCl$_3$) 60 MHz. δ 7.35–6.40 (m, 4H); 7.25 (s, 5H); 4.60–3.20 (m, 4H).

DESCRIPTION 11

1-(2,3-Dihydro-3-phenyl)indolylcarbonyl chloride (D11)

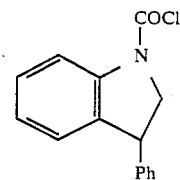

Following the procedure outlined in Description 6, reaction of 2,3-dihydro-3-phenylindole (D10) (2 g) with phosgene [9.2 ml (12.5% w/w solution in toluene)] and triethylamine (1.43 ml) afforded the title compound (D11) (1.6 g, 60%).

$^1$H-NMR (CDCl$_3$) 60 MHz. δ 8.20–7.90 (m, 1H); 7.58–6.80 (m, 8H); 4.85–3.98 (m, 3H).

DESCRIPTION 12

Spiro(cyclopentyl-3-indoline) (D12)

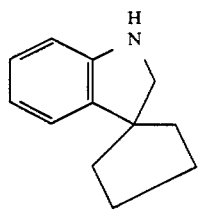

A solution of spiro(cyclopentyl-1,3-indolenine)trimer (1.1 g) (A. H. Jackson and B. Naidoo, Tetrahedron, 25, 4848–4852, 1969) in glacial acetic acid (20 ml) was hydrogenated over platinum oxide (0.22 g) at ambient temperature. After absorption of the theorectical amount of hydrogen (144 ml), the catalyst was filtered off and the solvent evaporated under reduced pressure. The residue was dissolved in 2N HCl (15 ml) and washed with diethyl ether (30 ml). The aqueous phase was basified with potassium carbonate and the product extracted into dichloromethane (2×50 ml). The organic phase was dried (Na₂SO₄) and the solvent evaporated under reduced pressure. The product was purified by distillation at reduced pressure to give the title compound (D12) (0.35 g, 32%).

¹H-NMR (CDCl₃) 60 MHz. δ 7.50–6.90 (m, 4H); 4.00–3.20 (m, 1H); 3.05 (m, 2H); 2.10–0.70 (m, 8H).

DESCRIPTION 13

Spiro(cyclopentyl-3-indoline)-1-carbonylchloride (D13)

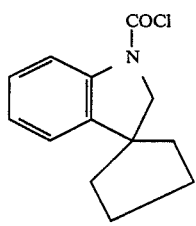

Following the procedure outlined in Description 6, reaction of spiro(cyclopentyl-3-indoline) (D12) (0.35 g) with phosgene [1.82 ml (12.5% w/w solution in toluene)] and triethylamine (0.28 ml) afforded the title compound (D13) (0.44 g, 92%).

¹H-NMR (CDCl₃) 60 MHz. δ 8.00–7.55 (m, 1H); 7.50–6.55 (m, 3H); 3.90 (s, 2H); 2.85–0.90 (m, 8H).

EXAMPLE 1

(endo)-N-(8-Methyl-8-azabicyclo]3,2,1]oct-3-yl)-N-[spiro(cyclohexyl-3-indolin-1-yl)]urea (E1)

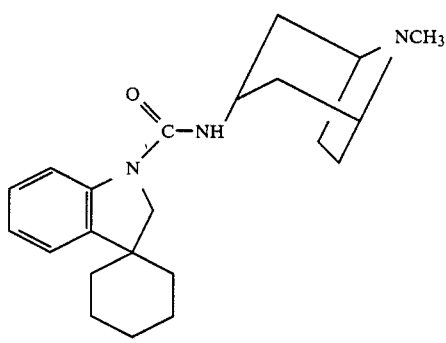

To a stirred solution of spiro(cyclohexyl-3-indoline)-1-carbonyl chloride (0.7 g) in CH₂Cl₂ (50 ml) at ambient temperature was added (endo)-8-methyl-8-azabicyclo[3,2,1]octan-3-amine (0.5 g) and triethylamine (0.5 ml). The reaction mixture was stirred at room temperature overnight. The resulting solution was washed with saturated NaHCO₃ solution, dried over Na₂SO₄ and the solvent removed by rotary evaporation to yield approximately 1 g of the crude title compound. This was subjected to column chromatography on neutral alumina (30 g) elution with CH₂Cl₂. The resulting product was crystallised from EtOAc/petrol to give the title compound (E1) (0.49 g, 49%).

m.p. 188°–190° C.

¹H-NMR (CDCl₃, 270 MH₂). δ 7.55 (d, 1H); 6.98–6.67 (m, 3H); 4.80 (brd, 1H); 3.91–3.82 (m, 1H); 3.48 (s, 2H); 2.95 (brs, 2H); 2.10–1.90 (m, 7H including 2.06, s, 3H); 1.65–1.05 (m, 14H).

EXAMPLE 2 endo-N-(8-Methyl-8-azabicyclo[3.2.1]oct-3-yl)2,3-dihydro-3-ethoxycarbonylindol-1-yl-urea hydrochloride (E2)

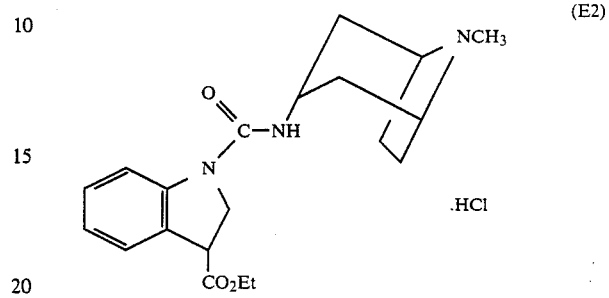

To 1-(2,3-dihydro-3-ethoxycarbonyl)indolylcarbonyl chloride (D6) (0.55 g) in dry dichloromethane (50 ml) was added dropwise a mixture of (endo)-8-methyl-8-azabicyclo [3.2.1]octan-3-amine (0.3 g) and triethylamine (0.3 ml) in dry dichloromethane (25 ml). The reaction mixture was stirred at room temperature overnight, the solvent was then evaporated under reduced pressure. The residue dissolved in 5N hydrochloric acid solution (20 ml) and washed with diethyl ether (50 ml). The aqueous phase was basified with potassium carbonate and then the product was extracted into dichloromethane (3×50 ml). The organic phase was dried (Na₂SO₄), the solvent was evaporated under reduced pressure and the residue filtered through a short alumina column eluting with 25% dichlomethane and 75% chloroform. The product was isolated as the hydrochloride salt (E2) (0.62 g) m.p. 230°–1° dec.

¹H-NMR (d₆-DMSO) 270 MHz. δ 10.75–10.40 (bs, 1H); 7.80 (d, 1H); 7.30 (d, 1H); 7.18 (t, 1H); 6.90 (t, 1H); 6.52 (s, 1H); 4.48–4.28 (m, 2H); 4.25–4.10 (m, 3H); 3.90–3.65 (m, 3H); 2.65 (s, 3H); 2.55–1.95 (m, 8H); 1.25 (t, 3H).

EXAMPLE 3 endo-N-(8-Methyl-8-azabicyclo[3.2.1]oct-3-yl)2,3-dihydro-3-ethoxycarbonyl-3-methylindol-1-yl urea (E3)

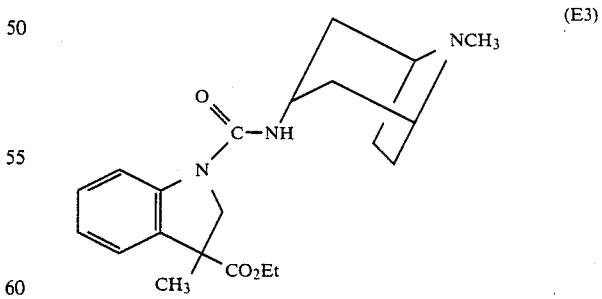

Following the procedure outlined in Example 2, reaction of 1-(2,3-dihydro-3-ethoxycarbonyl-3-methyl)indolylcarbonyl chloride (D7) (0.8 g) with (endo)-8-methyl-8-azabicyclo[3.2.1]octan-3-amine (0.42 g) and triethylamine (0.42 ml) afforded, after crystallisation from ethyl acetate and diethyl ether, the title compound (E3) (0.43 g, 39%), m.p. 119°–20° C.

¹H-NMR (CDCl₃) 270 MHz. δ 7.86 (d, 1H); 7.35 (dd, 1H); 7.30–7.19 (m, 1H); 6.96 (dt, 1H); 4,88 (bd, 1H); 4.58 (d, 1H); 4.27–4.15 (q, 2H); 4.15–4.02 (q, 1H); 3.60 (d, 1H); 3.28–3.10 (m, 2H); 2.38–2.05 (m, 4H); 2.31 (s, 3H); 1.93–1.67 (m, 4H); 1.63 (s, 3H); 1.28 (t, 3H).

EXAMPLE 4

(endo)-N-(8-Methyl-8-azabicyclo[3.2.1]oct-3-yl)2,3-dihydro-3-hydroxycarbonyl-3-methylindol-1-yl urea hydrochloride (E4)

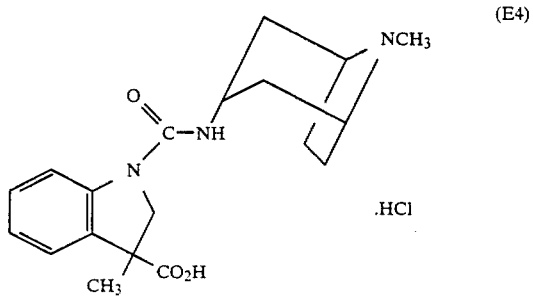

(endo)-N-(8-Methyl-8-azabicyclo[3.2.1]oct-3-yl)2,3-dihydro-3-ethoxycarbonyl-3-methylindole-1-carboxamide (E3) (0.32 g) was dissolved in 5N hydrochloric acid (15 ml) and stirred at ambient temperature for 18 h. The solvent was evaporated under reduced pressure and the residue re-evaporated with toluene (2×30 ml). The product was triturated with dry diethyl ether to give the title compound (E4) (0.31 g, 95%). m.p. 293°–6° C.

¹H-NMR (d₆-DMSO) 270 MHz. δ 10.88–10.52 (m, 1H); 7.78 (d, 1H); 7.28 (d, 1H); 7.16 (t, 1H); 6.92 (t, 1H); 6.48 (s, 1H); 4.55 (d, 1H); 3.95–3.40 (m, 5H); 2.62 (d, 3H); 2.58–1.95 (m, 8H); 1.52 (s, 3H); 1.93–1.67 (m, 4H).

EXAMPLE 5

(endo)-N-(8-Methyl-8-azabicyclo[3.2.1]oct-3-yl)2,3-dihydro-3-N,N-dimethylaminocarbonyl-3-methylindol-1-yl urea hydrochloride (E5)

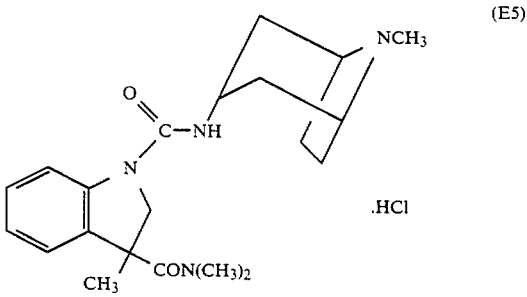

1-Hydroxybenzotriazole (0.06. g) in dry dimethylformamide (2 ml) was added to a stirred suspension of (endo)-N-(8-methyl-8-azabicyclo[3.2.1]oct-3-yl)2,3-dihydro-3-hydroxycarbonyl-3-methylindol-1-yl urea hydrochloride (E4) (0.15 g) in 50% dry dichloromethane/50% dry dimethylformamide (75 ml) at 0° C. 1,3-Dicyclohexylcarbodiimide (0.09 g) in 50% dry dichloromethane/50% dry dimethylformamide (10 ml) was added and the reaction mixture was stirred at 0° C. for 1½ h. Dimethylamine was bubbled through the suspension and the solution was then stirred at ambient temperature overnight. The solvent was evaporated under reduced pressure, the residue dissolved in dichloromethane and the dicyclohexylurea was filtered off. The filtrate was evaporated under reduced pressure, the residue dissolved in 5N hydrochloric acid (5 ml) and washed with diethyl ether (15 ml). The aqueous phase was basified with potassium carbonate and then extracted with dichloromethane (3×25 ml). The combined organic extracts were dried (Na₂SO₄) and the solvent was evaporated under reduced pressure. The residue was purified via column chromatography on neutral alumina (15 g) eluting with dichloromethane and chloroform. The product was isolated as the hydrochloride salt from ethyl alcohol and diethyl ether to give the title compound (E5) (0.063 g, 43%). m.p. 290°–2° C. dec.

¹H-NMR (d₆-DMSO) 270 MHz. δ 10.65–10.25 (m, 1H); 7.84 (d, 1H); 7.15 (t, 1H); 7.02 (d, 1H); 6.90 (t, 1H); 6.42 (bs, 1H); 4.34 (d, 1H); 3.92 (d, 1H); 3.90–3.65 (m, 3H); 3.00–2.50 (m, 9H); 2.50–1.90 (m, 8H); 1.42 (s, 3H).

EXAMPLE 6

(endo)-N-(8-Methyl-8-azabicyclo[3.2.1]oct-3-yl)-N'-[spiro(cyclopropyl-3-indolin-1-yl)urea (E6)

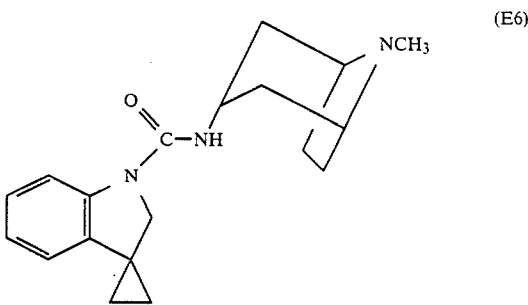

The title compound was prepared in an analogous manner to that of Example 1. m.p. 196°–1° C.

¹H-NMR (CDCl₃) 270 MHz. δ 7.82 (d, 1H); 7.13 (t, 1H); 6.88 (t, 1H); 6.61 (d, 1H); 4.90 (brd, 1H); 4.14–4.04 (m, 1H); 3.89 (s, 2H); 3.21–3.14 (brs, 2H); 2.29 (s, 2H); 2.28–2.10 (m, 4H); 1.82–1.68 (m, 4H); 1.12–1.02 (m, 4H).

EXAMPLE 7

(endo)-N-(8-Methyl-8-azabicyclo[3.2.1]oct-3-yl)2,3-dihydro-3-phenylindol-1-yl urea hydrochloride (E7)

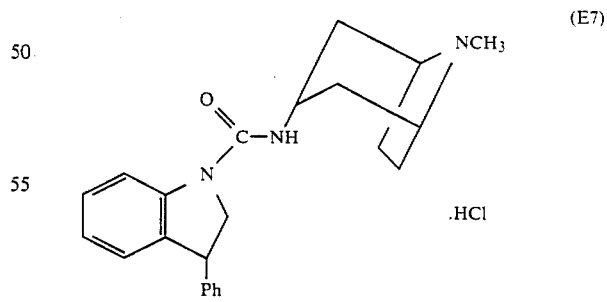

Following the procedure outlined in Example 1, reaction of 1-(2,3-dihydro-3-phenyl)indolylcarbonyl chloride (D11) (1g) with (endo)-8-methyl-8-azabicyclo[3.2.1]octan-3-amine (0.54 g) and triethylamine (0.54 ml) afforded, after addition of ethanolic-hydrochloride, the title compound (E7) (1.4 g, 91%) m.p. 319°–20° C. dec.

¹H-NMR (d₆-DMSO) 400 MHz. δ 10.40 (bs, 13H); 10.15 (bs, 0.87H); 7.88 (d, 1H); 7.35 (t, 2H); 7.28–7.18

(m, 3H); 7.13 (t, 1H); 6.93–6.80 (m, 2H); 6.33 (s, 1H); 4.65 (dd, 1H); 4.43 (t, 1H); 4.00 (dd, 1H); 3.80 (bs, 3H); 2.30 (d, 0.13H); 2.65 (d, 0.87H); 2.45–2.00 (m, 8H).

EXAMPLE 8

N-(1-Azabicyclo[2.2.2]oct-3-yl)2,3-dihydro-3-phenylindol-1-yl urea hydrochloride (E8)

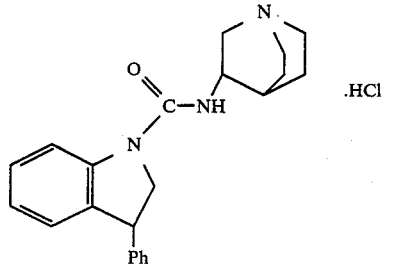

(E8)

To a solution of 1-azabicyclo[2.2.2]octan-3-amine dihydrochloride (0.46 g) in water (0.5 ml) was added dry dimethylformamide (15 ml) and triethylamine (0.65 ml). This mixture was stirred at room temperature for 5 min, then a solution of 1-(2,3-dihydro-3-phenyl)indolylcarbonyl chloride (D11) in dry dimethylformamide (20 ml) was added dropwise. The reaction mixture was stirred at room temperature for 18 h and then the solvent was evaporated under reduced pressure. The residue was dissolved in 5N hydrochloric acid solution (15 ml) and washed with diethyl ether (25 ml). The aqueous phase was basified with potassium carbonate and then extracted with dichloromethane (3×50 ml). The organic phase was dried ($Na_2SO_4$) and the solvent was evaporated under reduced pressure. The residue was filtered through a short alumina column, eluting with 25% dichloromethane/75% chloroform. The product was isolated as the hydrochloride salt (E8) (0.14 g, 16%) m.p. 313°–6° C. dec. as a mixture of diastereoisomers.

$^1$H-NMR (d$_6$-DMSO) 400 MHz. δ 9.98 (bs, 1H); 7.95–7.85 (2-d, 1H); 7.40–7.10 (m, 6H); 6.95–6.80 (m, 2H); 6.78–6.65 (m, 1H); 4.75–4.60 (dd, 1H); 4.50–4.35 (2-t, 1H); 4.20–4.05 (m, 1H); 3.98–3.83 (2-dd, 1H); 3.65–3.05 (m, 6H); 2.20–2.00 (m, 2H); 1.95–1.80 (m, 2H); 1.75–1.60 (m, 1H).

EXAMPLE 9

(endo)-N-(8-Methyl-8-azabicyclo[3,2,1]oct-3-yl)-3-phenylindol-1-yl urea hydrochloride (E9)

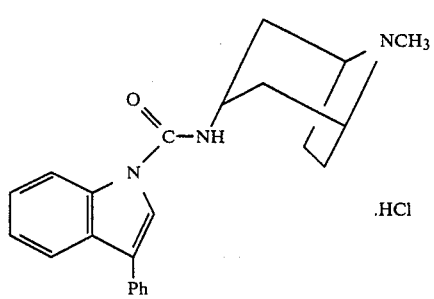

(E9)

(endo)-N-(8-Methyl-8-azabicyclo[3.2.1]oct-3-yl)-2,3-dihydro-3-phenylindol-1-yl urea hydrochloride (E7) (0.55 g) and 2,3-dichloro-5,6-dicyano-1,4-benzoquinone (0.38 g) in dry chloroform (100 ml) were heated under reflux for 6 h. The reaction mixture was cooled and washed with saturated potassium carbonate solution (20 ml). The organic phase was dried ($Na_2SO_4$), concentrated and the residue filtered through a short alumina column, eluting with chloroform. The product was isolated as the hydrochloride salt (0.22 g, 40%) m.p. 264°–5° C.

$^1$H-NMR (d$_6$-DMSO) 400 MHz. δ 10.50 (bs, 1H); 8.30 (b, 1H); 8.30 (d, 1H); 7.35 (d, 1H); 7.85 (d, 1H); 7.80–7.70 (m, 2H); 7.45–7.20 (m, 3H); 4.05–3.95 (m, 1H); 3.90–3.70 (m, 2H); 2.65 (bs, 3H); 2.60–2.10 (m, 8H).

EXAMPLE 10

(endo)-N-(8-Methyl-8-azabicyclo[3.2.1]oct-3-yl)-N'-[spiro(cyclopentyl-3-indolin-1-yl)urea (E10)

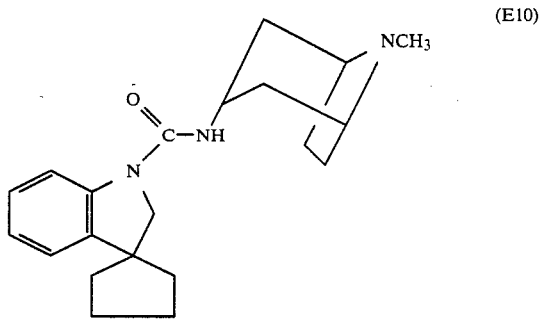

(E10)

The title compound was prepared in an analogous manner to that of Example 1.

m.p. 191°–3° C.

$^1$H-NMR (d$_6$-DMSO) 400 MHz. δ 7.80 (d, 1H); 7.25–7.05 (m, 2H); 6.95 (t, 1H); 4.95 (d, 1H); 4.15–4.00 (m, 1H); 3.65 (s, 2H); 3.25–3.15 (m, 2H); 2.30 (s, 3H); 2.35–2.10 (m, 4H); 2.00–1.65 (m, 12H).

PHARMACOLOGY

Antagonism of the von Bezold-Jarisch reflex

The compounds were evaluated for antagonism of the von Bezold-Jarisch reflex evoked by 5-HT in the anaesthetised rat according to the following method:

Male rats, 250–350 g, were anaesthetised with urethane (1.25 g/kg intraperitoneally) and blood pressure and heart rate recorded as described by Fozard J. R. et al., J. Cardiovasc. Pharmacol. 2, 229–245 (1980). A submaximal dose of 5-HT (usually 6 μg/kg) was given repeatedly by the intravenous route and changes in heart rate quantified. Compounds were given intravenously and the concentration required to reduce the 5HT-evoked response to 50% of the control response ($ED_{50}$) was then determined. Results were as follows:

| Compound | $ED_{50}$ μg/kg. |
|---|---|
| 1 | 3.6 |
| 6 | 3.5 |
| 8 | 1.2 |
| 10 | 1.8 |

We claim:

1. A compound of the formula (I), or a pharmaceutically acceptable salt thereof:

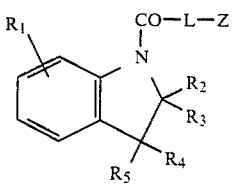 (I)

wherein

L is NH or O;

$R_1$ is hydrogen, fluoro or choloro;

$R_2$ and $R_5$ are independently hydrogen or $C_{1-6}$ alkyl or together are a bond; or one or both of $R_2$ and $R_3$, and $R_4$ and $R_5$, together are $C_{2-7}$ polymethylene or $-(CH_2)_m\text{-}O\text{-}(CH_2)_x\text{-}$ where m and x are 1 to 5 such that m+x is 2 to 6;

$R_3$ is hydrogen;

$R_4$ is $C_{1-7}$ alkanoyl, $C_{1-6}$ is alkoxycarbonyl, hydroxycarbonyl, aminocarbonyl optionally substituted by one or two $C_{1-6}$ alkyl groups, $CF_3$, $C_{1-6}$ alkyl substituted by $C_{1-6}$ alkoxy, $C_{1-6}$ alkylthio or by $C_{1-6}$ alkoxycarbonyl, or $R_4$ is phenyl or phenyl-$C_{1-4}$ alkyl optionally substituted in the phenyl ring by one or two of halogen, $C_{1-6}$ alkyl or $C_{1-6}$ alkoxy;

Z is a group of formula (a), (b), or (c)

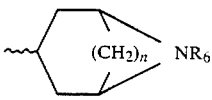 (a)

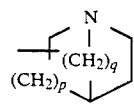 (b)

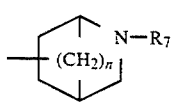 (c)

wherein n is 2 or 3;

p is 1 or 2;

q is 1 to 3;

r is 1 to 3; and $R_6$ or $R_7$ is $C_{1-4}$ alkyl.

2. A compound according to claim 1 of formula (II):

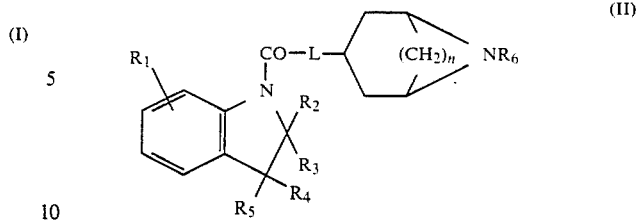 (II)

wherein $R_1$ to $R_6$, L and n are as defined in claim 1.

3. A compound according to claim 2 wherein $R_6$ is methyl and Z is in the endo configuration.

4. A compound according to claim 1 of formula (III):

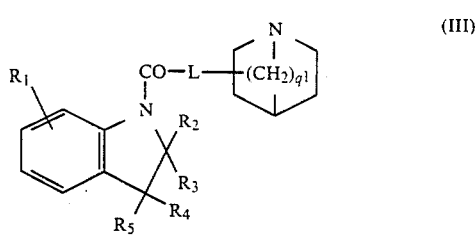 (III)

wherein $q^1$ is 1 or 2 and $R_1$ to $R_5$ and L are as defined in claim 1.

5. A compound according to claim 1 wherein L is NH.

6. A compound according to claim 1 wherein $R_1$ is hydrogen.

7. A compound selected from the group consisting of
(endo)-N-(8-methyl-8-azabicyclo(3,2,1)oct-3-yl)-N-(spiro(cyclohexyl-3-indolin-1-yl))urea,
(endo)-N-(8-methyl-8-azabicyclo(3.2.1)oct-3-yl)2,3-dihydro-3-ethoxycarbonylindol-1-yl-urea,
(endo)-N-(8-methyl-8-azabicyclo(3.2.1)oct-3-yl)2,3-dihydro-3-ethoxycarbonyl-3-methylindol-1-yl urea,
(endo)-N-(8-methyl-8-azabicyclo(3.2.1)oct-3-yl)2,3-dihydro-3-hydroxycarbonyl-3-methylindol-1-yl urea,
(endo)-N-(8-methyl-8-azabicyclo(3.2.1)oct-3-yl)2,3-dihydro-3-N,N-dimethylaminocarbonyl-3-methylindol-1-yl urea,
(endo)-N-(8-methyl-8-azabicyclo(3.2.1)oct-3-yl)-N'-[spiro(cyclopropyl-3-indolin-1-yl)]urea,
(endo)-N-(8-methyl-8-azabicyclo(3.2.1)oct-3-yl)2,3-dihydro-3-phenylindol-1-yl urea,
N-(1-azabicyclo(2.2.2)oct-3-yl)2,3-dihydro-3-phenylindol-1-yl urea,
(endo)-N-(8-methyl-8-azabicyclo(3,2,1)oct-3-yl)-3-phenylindol-1-yl urea,
(endo)-N-(8-methyl-8-azabicyclo(3.2.1)oct-3-yl)-N'-(spiro(cyclopentyl-3-indolin-1-yl))urea,
and pharmaceutically acceptable salts of any of the foregoing.

8. A pharmaceutical composition for use in the treatment of migraine, cluster headaches, trigeminal neuralgia, emesis or visceral pain, comprising an effective amount of a compound according to claim 1, and a pharmaceutically acceptable carrier.

9. A method of treatment of migraine, cluster headaches, trigeminal neuralgia, emesis or visceral pain, which comprises the administration of an effective amount of a compound according to claim 1.

* * * * *